United States Patent
Miao

(10) Patent No.: US 9,896,727 B2
(45) Date of Patent: Feb. 20, 2018

(54) REGULATOR TARGETTING FATTY ACID SYNTHASE AND METHOD OF USING THE SAME FOR IMPROVING MEAT QUALITY

(71) Applicant: Xiangyang Miao, Beijing (CN)

(72) Inventor: Xiangyang Miao, Beijing (CN)

( * ) Notice: Subject to any disclaimer, the term of this patent is extended or adjusted under 35 U.S.C. 154(b) by 0 days.

(21) Appl. No.: 14/859,374

(22) Filed: Sep. 21, 2015

(65) Prior Publication Data

US 2016/0083790 A1 Mar. 24, 2016

(30) Foreign Application Priority Data

Sep. 19, 2014 (CN) .......................... 2014 1 0480211

(51) Int. Cl.
 *C12N 15/113* (2010.01)
 *C12Q 1/68* (2006.01)

(52) U.S. Cl.
 CPC .......... *C12Q 1/6876* (2013.01); *C12N 15/113* (2013.01); *C12N 2310/141* (2013.01); *C12Q 2600/124* (2013.01); *C12Q 2600/158* (2013.01); *C12Q 2600/178* (2013.01)

(58) Field of Classification Search
 None
 See application file for complete search history.

(56) References Cited

PUBLICATIONS http://www.mirbase.org/help/nomenclature.shtml, downloaded from the web on Aug. 21, 2016.*
Persson et al (Cancer Res; 71(1) Jan. 1, 2011), and Supplementary Material 4.*
Thompson et al (Meat Science 74 (2006) 59-65).*
Sheng et al (Mol. Biol. Reports 38(5(: 3161-3171, 2011).*
Ambros et al (RNA (2003), 9:277-279).*
miRBase entry for has-miR-4749 retrieved from http://www.mirbase.org/cgi-bin/mirna_entry.pl?acc=MI0017388 on Aug. 21, 2016.*
Laliotis et al (Current Genomics, 2010, 11, 168-183).*

\* cited by examiner

*Primary Examiner* — Richard A Schnizer
(74) *Attorney, Agent, or Firm* — Matthias Scholl, PC; Matthias Scholl

(57) ABSTRACT

A miRNA miR-4749-5 represented by the sequence of SEQ ID NO: 1 is disclosed.

4 Claims, 1 Drawing Sheet

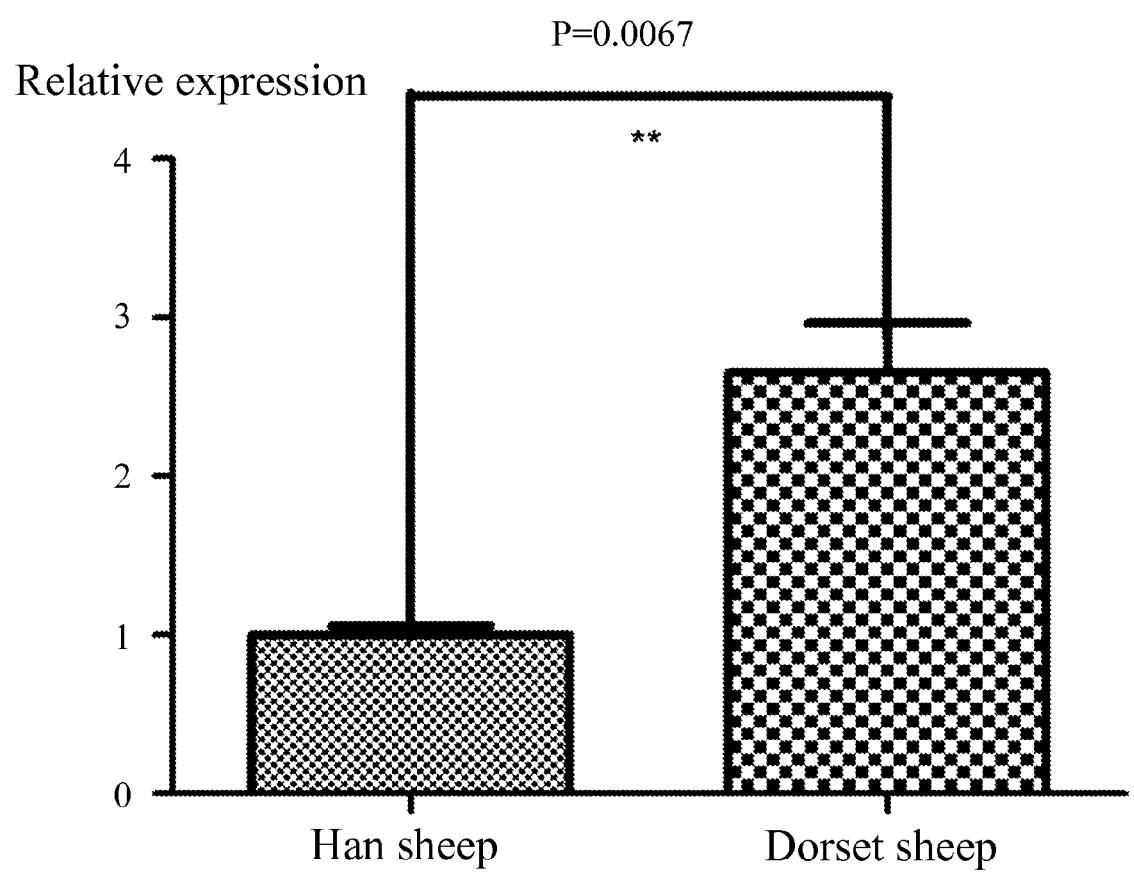

SEQUENCE LISTING

<160> NUMBER OF SEQ ID NOS: 7

<210> SEQ ID NO 1
<211> LENGTH: 19
<212> TYPE: RNA
<213> ORGANISM: Artificial Sequence
<220> FEATURE:
<223> OTHER INFORMATION: Fully synthetic

<400> SEQUENCE: 1 ccugucccg ccuucaccc                                               19

<210> SEQ ID NO 2
<211> LENGTH: 50
<212> TYPE: DNA
<213> ORGANISM: Artificial Sequence
<220> FEATURE:
<223> OTHER INFORMATION: Fully synthetic

<400> SEQUENCE: 2
gtcgtatcca gtgcagggtc cgaggtattc gcactggata cgacgggtga             50

```
<210> SEQ ID NO 3
<211> LENGTH: 22
<212> TYPE: DNA
<213> ORGANISM: Artificial Sequence
<220> FEATURE:
<223> OTHER INFORMATION: Fully synthetic

<400> SEQUENCE: 3
tatcctgtcc ccgccttcac cc                                          22

<210> SEQ ID NO 4
<211> LENGTH: 22
<212> TYPE: DNA
<213> ORGANISM: Artificial Sequence
<220> FEATURE:
<223> OTHER INFORMATION: Fully synthetic

<400> SEQUENCE: 4
cagtgcaggg tccgaggtat tc                                          22

<210> SEQ ID NO 5
<211> LENGTH: 19
<212> TYPE: DNA
<213> ORGANISM: Artificial Sequence
<220> FEATURE:
<223> OTHER INFORMATION: Fully synthetic

<400> SEQUENCE: 5
cctgtccccg ccttcaccc                                              19

<210> SEQ ID NO 6
<211> LENGTH: 17
<212> TYPE: DNA
<213> ORGANISM: Artificial Sequence
<220> FEATURE:
<223> OTHER INFORMATION: Fully synthetic

<400> SEQUENCE: 6
ctcgcttcgg cagcaca                                                17

<210> SEQ ID NO 7
<211> LENGTH: 20
<212> TYPE: DNA
<213> ORGANISM: Artificial Sequence
<220> FEATURE:
<223> OTHER INFORMATION: Fully synthetic

<400> SEQUENCE: 7
aacgcttcac gaatttgcgt                                             20
```

REGULATOR TARGETTING FATTY ACID SYNTHASE AND METHOD OF USING THE SAME FOR IMPROVING MEAT QUALITY

CROSS-REFERENCE TO RELATED APPLICATIONS

Pursuant to 35 U.S.C. § 119 and the Paris Convention Treaty, this application claims the benefit of Chinese Patent Application No. 201410480211.X filed Sep. 19, 2014, the contents of which are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

Field of the Invention

The invention relates to a regulator targeting fatty acid synthase and method of using the same for improving meat quality.

Description of the Related Art miRNAs are a group of endogenous non-coding single-stranded RNA molecules containing between 19 and 24 nucleotides. miRNAs are highly conservative and able to form specific complementary base pairs with target mRNAs, which results in decomposition or translation inhibition of the target mRNAs.

With the improvement of sheep breeding, the sheep meat quality is decreased. The meat quality trait is related to the content and the constituent of fatty acids and controlled by minor genes, and requires molecular markers related to the fatty acid synthesis to regulate. Gene of fatty acid synthase (FAS) (gene that encodes FAS) plays a key role in regulating the synthesis of fatty acids. The synthesis rate of fatty acids can be regulated by regulating the expression and the activity of FAS gene, thus affecting the meat quality trait. So, to improve the sheep meat quality, a molecular marker adapted to regulate the expression of FAS gene is required.

SUMMARY OF THE INVENTION

In view of the above-described problem, it is one objective of the invention to provide a miRNA marker adapted to improve the sheep meat quality. The miRNA is miR-4749-5 of sheep.

It is another objective of the invention to provide a sequence of the miRNA represented by SEQ ID NO: 1: CCUGUCCCCGCCUUCACCC.

It is still another objective of the invention to provide a target gene of the above miRNA, and the target gene is FAS gene.

In a class of this embodiment, the miRNA is expressed at a low level in an adipose tissue of a fine meat sheep variety, such as a Han sheep.

It is still another objective of the invention to provide a primer for the miRNA marker.

In a class of this embodiment, when a stem-loop method is adopted to detect the miRNA marker, a sequence of a reverse transcription (RT) primer is represented by SEQ ID NO: 2, a forward primer is represented by SEQ ID NO: 3, and a reverse primer is represented by SEQ ID NO: 4.

In a class of this embodiment, a probe method or a dye method is adopted when using the stem-loop method to detect the miRNA marker.

In a class of this embodiment, when a tailing method is used to detect the miRNA marker, a forward primer is represented by SEQ ID NO: 5.

A real-time fluorescence quantitative PCR (Q-PCR) kit is prepared for detecting an expression of the miRNA. The Q-PCR kit comprises: a reverse transcription (RT) reagent, an RT primer, a specific primer for amplifying miR-4749-5, an internal control primer, and a reaction solution for Q-PCR. Preferably, the Q-PCR kit further comprises a specific probe. Preferably, a sequence of the RT primer is represented by SEQ ID NO: 2. The specific primer comprises a forward primer and a reverse primer. The forward primer has a sequence of SEQ ID NO: 3, and the reverse primer has a sequence of SEQ ID NO: 4. The internal control primer is a U6 internal control primer.

A Q-PCR kit prepared for detecting the expression of the miRNA comprises: an RT reagent, an RT primer, a specific forward primer, a universal reverse primer, an internal control primer, and a reaction solution for the Q-PCR. A sequence of the specific forward primer is represented by SEQ ID NO: 5.

The above kits are applied in quantitative detection of the miRNA in the adipose tissue of the sheep.

To achieve the above purpose, Han sheep and Dorset sheep are herein utilized as the experimental materials. Adipose tissue samples are respectively collected from five Dorset sheep and five Han sheep and sent to a sequencing company for high-throughput transcriptome sequencing. The sequencing results are combined with an internationally accepted algorithm EBSeq to analyze the differential gene expression. The obviously differentially expressed miR-4749-5 is selected through analysis, a sequence of which is represented by SEQ ID NO 1 miR-4749-5 is further used as the study object, and FAS is predicted to be the target gene regulated by miR-4749-5 by searching the RNA hybrid data bank.

The primer sequence is devised according to the above miRNA sequence and the FAS sequence.

Expressions of miR-4749-5 and FAS in the adipose tissues selected from 45 Dorset sheep and 45 Han sheep are detected by RT-PCR method, respectively, and results indicate that the expression of miR-4749-5 in the adipose tissue of the Dorset sheep is obviously higher than that of the Han sheep, and the former is approximately 2.65 times of the later.

The experimental results of the inhibition of the expression of gene FAS by miR-4749-5 indicate that miR-4749-5 is able to negatively regulate the gene FAS, which indicates that miR-4749-5 can be used as a marker for the generic breeding related to the sheep meat quality.

It is still another objective of the invention to provide a detection kit for detecting the miRNA marker and/or detecting the target gene FAS. The PCR kit is applicable for all types of fluorescent quantitative gene amplification apparatuses in the current market, and has high sensitivity, fast and accurate quantitation, excellent stability, and good application prospect.

It is still another objective of the invention to provide a method for detecting miR-4749-5.

The method for detecting miR-4749-5 adopts a method based on nucleotide hybridization (such as Northern blot, in situ hybridization, bead-based flow-cytometry, and microarray), splinted ligation, and methods based on PCR (such as RNA tailing, small target quantitative PCR, and stem-loop method), or a combination thereof.

Northern blot is generally conducted as follows: extracting a small RNA having a length of approximately within 200 bp from a total RNA using polyacrylamide gel electrophoresis, transferring the small RNA to a blotting membrane to hybridize with a labeled oligonucleotide probe, and analyzing a band after washing and developing the membrane. In order to improve the affinity and the detection sensitivity of the hybridization reaction, a locked nucleic acid (LNA) probe is applied in the analysis research of the miRNA. It is known from the experiment that the introduction of each LNA-modified base into the oligonucleotide probe will result in an increase of between 1 and 8° C. in a melting temperature during hybridization with corresponding DNA, and an increase of between 2 and 10° C. in a melting temperature during hybridization with RNA, so that the hybridization specificity and the sensitivity between the LNA probe and the miRNA molecules are improved.

miRNAs in situ hybridization is a kind of hybridization that utilizes a colorimetric reagent or a fluorescent reagent labeled DNA probe to hybridize with miRNAs in cells or tissues, and detects the expression of miRNAs via coloration or fluorescence imaging so as to directly show the spatiotemporal expression of miRNAs. The in situ hybridization is capable of displaying the position of the miRNA expression, or even reaching the cell positioning level, therefore being more particularly suitable for paraffin embedded or Formalin fixed specimens.

The bead-based flow-cytometry, i. e., the multi-analyte suspension assay, is a technique that organically combines the flow cytometry with the chip technology, to transform the biochip reaction system from the liquid-solid reaction into a total liquid-phase reaction system which is the most similar to the inner environment of the biological system. Such method utilizes polystyrene beads as reaction carriers, and different beads are labeled with different fluorescent codings that can be identified by corresponding detection systems. The bead can be connected to DNA probes or proteins. The bead is connected to a miRNA capturing probe having a length of between 10 and 12 nt when it is supposed to detect the miRNA. The probe is complementary to the 3'-end of the miRNA and is added with a reporter probe having a length of between 8 and 10 nt to react with the 5'-end of the miRNA. After the reaction, the classified fluorescence of the probes and the labeled fluorescence of the reporter probe on the beads are detected by two laser beams, respectively, in the detection system, thereby realizing the qualitative and quantitative detections of the target miRNA.

The microarray technology is also called the biochip, DNA chip, or gene chip technology. Generally, DNA probes with known sequences in high density arrangement are fixed on a solid supporting material, such as a glass piece, multiple miRNAs target molecules are hybridized with the microarray based on the hybridization principles. By detecting the hybridization signal intensity and processing the data, expression profiles of the specific miRNAs in different specimens are acquired, so that differences in the miRNAs expressions are comprehensively compared between different organs or tissues and between normal tissues and pathological tissues. The microarray technology is advantageous in high throughput, i. e., the whole genome can be analyzed for once, and expressions of more than thirty thousand of genes can be quantitatively acquired in ten minutes.

In the splinted-ligation technique, a segment of deoxynucleotide (a bridge fragment) is pre-designed, and this bridge fragment comprises a 14 nt extension segment at the 5'-end as well as a 3'-end complementary to the target miRNA. In addition, a second depxynucleotide segment (junction fragment) complementary to the 14 nt extension segment is devised, and a 5'-end thereof is labeled with $32^P$. During the annealing, the miRNA and the junction fragment are simultaneously complementary with the bridge fragment, so that a heteroduplex is produced, and a gap exists in the middle of one strand, that is, the juncture between miRNA and the junction fragment. The gap is repaired by a T4DNA ligase, which is equivalent to label miRNA with $32^P$. Free junction fragment labeled by $32^P$ is removed by phosphatase, and polyacrylamide gel electrophoresis is then carried out. The intensity of the radioactive signal is detected, so as to acquire the information corresponding to the amount of miRNA. This method is much simpler, faster, and more sensitive than the Northern blot and can be used to carry out detection of a large amount of specimen.

Tailing method. miRNA has a length of only 22 nt, which is only corresponding to the length of a primer, so that miRNA cannot be detected by conventional RT-PCR. miRNA can be detected using RNA tailing and primer extension RT-PCR. The total RNA is firstly extracted, followed with the small RNA. A segment of the poly A is added at the 3'-end of the small RNA as a tail by the poly A polymerase, and miRNA is reversely transcribed into cDNA by a long primer with a 3'-end containing a segment of poly T. The length of the acquired cDNA is suitable for Q-PCR.

The small target quantitative PCR comprises three steps: reverse transcription, connecting to a DNA template, and PCR amplification of a connecting product. Each reaction is separated from another reaction by deactivation. During the reverse transcription, miRNA is reversely transcribed into cDNA by the specific primer. Because miRNAs are different in at least one base, and the differences are mostly in the 3'-end of miRNA, thus, the terminal of the primer should be within the hypervariable (HVR) region or the vicinity thereof at the 3'-end of miRNA and the length of the primer should be as short as possible. In the second step of the reaction, the cDNA is complementary pairing with the two oligonucleotides, and after the complementary pairing, the gap between the two oligonucleotides reaches the length of 7 nucleotides. Each oligonucleotide is partially pairing to the cDNA, and the remaining part exceeding the length of the cDNA is exposed, which is called M13+. The gap is then filled by T4 DNA ligase, the connecting reaction is very sensitive to the mis-match of the bases at the two ends of the gap, particularly the 3'-end, therefore, the 3'-end of the gap should be arranged at the HVR region of the miRNA to the utmost. In the third reaction, PCR amplification is performed using the connecting product as the template, the forward primer and the reverse primer of the M13+ as the universal PCR primers, and the specific TaqMan probes. Because both the reverse transcription and the connecting reaction use the center of the miRNA and the 3'-end thereof that is the main region to distinguish the miRNA member as the specific target, and the T4 DNA ligase is capable of distinguishing the mismatch of the bases, thus, such the method has relatively high specificity, low cross reaction rate, and can be used as the method for quantitatively detecting the sensitivity of the short nucleotide.

The stem-loop method features in using a single stem-loop primer to avoid tailing the target miRNA. The reaction process is divided into two steps: first, the stem-loop primer is combined with the 3'-end of the target miRNA molecule, 6 complementary base pairings are formed at the 3'-end of the primer and the 3'-end of the miRNA, and the miRNA is then reversely transcribed into a first strand of cDNA by the reverse transcriptase; and second, the PCR reaction is performed. The strand length is increased when the stem-loop structure of the first strand of the cDNA is expanded, and the conventional Q-PCR is performed using the expanded stem-loop structure as the template. The stem part of the stem-loop primer is in a double-strand structure preventing the primer to hybridize with the pre-miRNA or other long stranded RNA. The base stacking at the stem part enhances the affinity of a miRNA-DNA heteroduplex, thereby improving the efficiency of the reverse transcription. The length of the miRNA is increased after the expansion of the stem-loop structure, and then the miRNA participates in the PCR working as a suitable template.

In a class of this embodiment, the expression of miR-4749-5 is detected by fluorescent quantitation.

In a class of this embodiment, the expression of miR-4749-5 is detected by the tailing method of the RT-PCR.

In a class of this embodiment, the tailing method for detecting the expression of miR-4749-5 comprises the following steps: 1) extracting the small RNAs from the adipose tissue of the sheep; 2) tailing and reversely transcribing miR-4749-5 using a poly(A) polymerase and a reverse transcriptase; and 3) amplifying miR-4749-5 using SEQ ID NO: 5 and a commercially available Q-PCR kit applicable for the tailing method.

In a class of this embodiment, the tailing method for detecting the expression of miR-4749-5 comprises the following steps: 1) extracting the small RNAs from the adipose tissue of the sheep; 2) tailing and reversely transcribing miR-4749-5 using a miScript II RT kit provided by Qiagen; and 3) amplifying miR-4749-5 using the SEQ ID N: 5 and a miScript SYBR Green PCR Kit provided by Qiagen.

In a class of this embodiment, the stem-loop method for detecting the expression of miR-4749-5 comprises the following steps: 1) extracting the total RNAs from the adipose tissue of the sheep; 2) reversely transcribing miR-4749-5 using SEQ ID NO: 2 as the RT primer under the action of a reverse transcriptase; and 3) amplifying miR-4749-5 using SEQ ID NO: 3 and SEQ ID NO: 4 as the primers and a commercially available Q-PCR kit suitable for the stem-loop method.

It is still another objective of the invention to provide a method for genetic marker-assisted breeding and improving the sheep meat quality comprising applying miR-4749-5 as a molecular marker.

In a class of this embodiment, in the method for genetic marker-assisted breeding and improving the sheep meat quality, miR-4749-5 is expressed at a low level in the adipose tissue of the target meat sheep.

Definitions of miRNA and Precursor Thereof

The invention provides a kind of miRNA relating to the sheep meat quality. As used in the invention, the "miRNA" is a group of small non-coding single strand RNA molecule containing approximately between 19 and 25 nucleotides and widely existing in plants, nematodes, drosophilas, and mammals. The miRNA mainly combines with a 3'-UTR region of the encoding protein mRNA via the basically complementary mode to cause the degradation, activity decrease, or translation inhibition of the target mRNA, so as to regulate a group of RNA molecules via the gene expression after the transcription. The mature miRNA generally contains between 19 and 25 nucleotides (nt) (approximately between 19 and 22 for special ones), while other nucleotide numbers are not excluded.

miRNA can be obtained by processing a precursor miRNA (pre-miRNA). The pre-miRNA can be folded into a stable stem-loop (hairpin) structure. The stem-loop structure generally has a length of between 50 and 100 bp. The pre-miRNA can be folded into a stable stem-loop structure. Two sides of the stem part of the stem-loop structure contain two basically complementary sequences. The pre-miRNA is natural or artificial.

The pre-miRNA can be cut into miRNA. The miRNA is basically complementary to at least one part of the sequence of the gene encoding miRNA. Herein, the "basically complementary" means that the two nucleotide sequences are sufficiently complementary and interact with each other in a predictable mode, for example, forming a secondary structure such as the stem-loop structure. Generally, at least 70% of the nucleotides in the two basically complementary nucleotide sequences are complementary to each other; preferably, at least 80% of the nucleotides of the two sequences are complementary; and more preferably, the proportion reaches 90%; and still more preferably, the proportion reaches at least 95%, such as 98%, 99%, and 100%. Generally speaking, at most 40 unmatched nucleotides are permitted to exist in the two sufficiently complementary molecules; preferably, at most 30 unmatched nucleotides exist; more preferably, at most 20 unmatched nucleotides exist; and more preferably, at most 10 unmatched nucleotides exist, for example, 1, 2, 3, 4, 5, 8, and 11 unmatched nucleotides exist.

The stem-loop structure is also called the hairpin structure, which means a nucleotide molecule capable of forming a secondary structure containing a double-strand region (the stem part). The double-strand region is formed by two regions of the same nucleotide molecule, and the two regions are arranged at two sides of the double-strand region. Furthermore, the hairpin structure further comprises a loop structure, which comprises a noncomplementary nucleotide sequence, i. e., the single strand region. Even the two regions of the nucleotide molecule are not totally complementary to each other, and the double-strand region of the nucleotide molecule is able to remain the double-strand state. Such as, insertion, deletion, substitution, etc., may lead to dismatch in a small region, self-formation of a stem-loop structure or other secondary structure in the small region. However, the two regions are basically complementary to each other, and interact with each other in a predictable mode, and form the double-strand region in the stem-loop structure. The stem-loop structure is well-known by the persons skilled in the art, and generally the persons skilled in the art are able to determine whether the nucleotide is able to form the stem loop structure after the nucleotide sequence in a primary structure is acquired.

Small RNA Sequencing

The small RNA is a group of important regulatory molecules in vivo, and primarily comprises: miRNA, piRNA, and siRNA. The main function thereof is inducing gene silencing, involving in post-transcriptional gene regulation, and therefore regulating the important biological processes such as the cell growth, differentiation, ontogeny, and reproduction. The small RNA sequencing technology adopts the gel extraction technology, between 18 and 30 nt RNA segments are collected from the sample, and high throughput sequencing technology is adopted to acquire information of millions of small RNA sequences of the single-base resolution for one time. The known small RNA is identified, relying on a strong bioinformatics analysis platform, and the new small RNA and the target gene thereof are predicted.

miRNA herein further comprises a miRNA variant and a derivative thereof. In addition, the general miRNA derivative comprises the miRNA variant. Persons skilled in the art are able to modify the miR-4749-5 using universal method. The modification comprises: methylation modification, hydrocarbon modification, glycosylation modification (e.g.

2-methoxy-glycosyl modification, hydrocarbon-glycosyl modification, sugar-ring modification, etc.), nucleic acid modification, peptide modification, lipid modification, halogen modification, nucleic acid modification like "TT" modification, and others.

Construct of Polynucleotide

According to the miRNA sequence provided in the invention, a polynucleotide construct of the miRNA is devised and the polynucleotide construct is formed after introduction and is able to affect the expression of the corresponding mRNA, that is, the polynucleotide construct is able to regulate the amount of the corresponding miRNA in vivo. The polynucleotide construct can be transcribed into the pre-miRNA by animal cells, and the pre-miRNA can be further cut and express the miRNA by the animal cells.

Generally, the polynucleotide construct is carried by the expression vector. Thus, the invention also provides a vector which comprises the miRNA or the polynucleotide construct. The expression vector generally comprises a promoter, and a replication origin, and/or a marker gene. The expression vector necessitated herein in the invention can be constructed using methods well-known by the persons skilled in the art, such as the in vitro recombinant DNA technology, the DNA synthesis techniques, and in vivo recombination technology, etc. The expression vector preferably comprises one or multiple selectable marker genes, so as to provide selectively convertible phenotypic traits of the host cells, such as resistances of kalamycin, gentamicin, hygromycin, and ampicillin.

The adipose tissues of the two sheep varieties are performed with the high-throughput transcriptome sequencing and the differential gene expression analysis via bioinformatics method so as to screen the miRNA related to the regulation of the expression of gene FAS in the sheep, which is named miR-4749-5. Results of further molecular biology experiments indicate that miRNA of the invention is capable of effectively regulating the expression of gene FAS and can be adopted as a miRNA molecular marker related to fatty acids in the sheep. In addition, the detection kit for detecting the molecular marker of the invention has important practical application value in genetic marker-assisted breeding in sheep.

Advantages according to embodiments of the invention are summarized as follows:

a) miR-4749-5 provided in the invention is well correlated with the sheep meat quality and is used in genetic marker-assisted breeding related to the sheep muscle quality.

b) The Q-PCR kit for detecting the expression of miR-4749-5 provided by the invention comprises the whole kits for experiments from RNA extraction to the fluorescent quantitation, which is not only convenient for use but also ensures the consistency of the results.

BRIEF DESCRIPTION OF THE DRAWINGS

The invention is described hereinbelow with reference to accompanying drawings, in which the sole FIGURE shows relative expression amounts of miR-4749-5 in adipose tissues of Dorset sheep and Han sheep detected by real-time PCR in accordance with one embodiment of the invention.

DETAILED DESCRIPTION OF THE EMBODIMENTS

For further illustrating the invention, experiments detailing a regulator targeting fatty acid synthase and method of using the same for improving meat quality are described below. It should be noted that the following examples are intended to describe and not to limit the invention.

Example 1 High-Throughput Transcriptome Sequencing for Differential Expression miRNA Profiling in Adipose Tissues of Different Sheep Varieties Adipose tissues were extracted from five Dorset sheep and five Han sheep, respectively. The tissue specimens were divided into small masses respectively and frozen in liquid nitrogen for 30 seconds, and then preserved in a refrigerator at a temperature of −70° C. Small RNA sequencing was performed by a sequencing company.

The quality of the sequencing data was integrally assessed using the Fast-QC software, and the integral assessment included the distribution of the mass value of the base, the position distribution of the mass value, the GC content, the PCR duplication content, the k-mer frequency, etc.

Analysis results of the mature small RNA having the sum of the counts smaller than 10 were deleted, and differential screen was performed combining with the internationally accepted algorithm EBSeq, in which log FC>1 or Log FC<−1, and FDR<0.05. Significantly differentially expressed miR-4749-5 was finally screened from the analysis, and the sequence thereof was SEQ ID NO: 1. It was predicted by searching the RNA hybrid data bank that the miR-4749-5 regulates the target gene FAS.

Example 2 Expression of miR-4749-5 in the Adipose Tissue of the Sheep Detected by Real-Time PCR Reagents:

RT reagent kit: SG One-Step miRNA RT Kit, #33-30120, SinoGene

PCR Mix: 2×SG PCR MasterMix, #33-10201, SinoGene qPCR reagent: 2×SG Green qPCR Mix (with ROX), #22-10102, SinoGene Treatment of experiment instruments for removing Rnase:

1) The laboratory glassware was washed and soaked with DEPC solution, and pressurized at 120° C. for 20 min, and then baked at 180° C. for more than 2 hrs; and 2) The plastic containers (such as EP tubes/pipet tips) were washed in 0.1% DEPC and soaked for overnight, naturally dried, pressurized at 120° C. for 20 min, and then baked.

The adipose tissue samples were extracted from 45 Dorset sheep and 45 Han sheep, numbered, and then the samples were randomly selected to extract the RNA.

miRNA Extraction:

1) The adipose tissue sample was taken out from the liquid nitrogen, weighed, and placed in centrifuge tubes. Trizol solution was added to the centrifuge tube according to between 50 and 100 mg of the tissue per mL of the amount of Trizol. The tissue volume was not allowed to exceed 10 v. % of the Trizol volume, and a mixture thereof was homogenized for between 1 and 2 min 2) The tissue added with the Trizol was incubated at between 15 and 30° C. for 5 min to make the tissue fully decomposed.

3) A miRNA homogenate additive having a volume of 1/10 of that of a mixture in the tube was added and then swirled for several times so as to uniformly mix a resulting mixture, and the centrifuge tube was placed on the ice for 10 min.

4) Trichloromethane having the same volume as that of resulting decomposed substances in the centrifuge tube was added, and swirled for between 30 and 60 s for uniform mixing.

5) The centrifuge tube was centrifuged for 5 min at the room temperature at a maximum rotational speed (10000 g), so as to separate a water phase from an organic phase and to separate out a middle phase. If the middle phase was not separated out, another centrifuging process was performed.

6) The water phase in the upper layer was sucked and transferred to a new collection tube, and a volume of the water phase water recorded.

7) Anhydrous alcohol having a volume of ⅓ of that of the water phase was added, and a mixed solution was swirled or inverted for several times for uniform mixing.

8) The decomposed solution/alcohol mixed solution was added to a filter core for filtration. The filter core was placed in a new collection tube, and each sample was provided with one filter core.

9) A pipet was used to transfer the mixed solution in the above step to the filter core having a volume capacity of 700 μL for once. Additional mixed solution exceeding 700 μL was continuously filtered by the same filter core.

10) The solution was allowed to pass through the filter core by centrifuging at a rotational speed of 10000 g for 15 s.

11) A filtrate was collected. If the volume of the decomposed solution/alcohol mixed solution was larger than 700 μL, a new collection tube was adopted in continuous filtration till all the decomposed solution/alcohol mixed solution was filtrated, the filtrate was collected, and the volume was recorded.

12) To the filtrate collected from the above step, anhydrous alcohol having a volume of ⅔ of that of the filtration was added at the room temperature.

13) The filtrate/alcohol mixed solution was added to a second filter core for filtration, a filtrate was discarded. Each sample was provided with a filter core, and the filter core is placed in a new collection tube.

14) A pipet was used to transfer the mixed solution in the above step to the filter core having a volume capacity of 700 μL for once. Additional mixed solution exceeding 700 μL was continuously filtered by the same filter core.

15) The solution was allowed to pass through the filter core by centrifuging at a rotational speed of 10000 g for 15 s.

16) A filtrate obtained from the filtration was discarded, and the filter core was kept for conducting elution in a subsequent step.

17) 700 μL of miRNA washing liquid 1 (alcohol was added to a working solution) was added to the filter core, and centrifuged for between 5 and 10 s. A liquid produced in the elution was discarded, and the collection tube was continuously used.

18) 500 μL of miRNA washing liquid ⅔ (alcohol was added to a working solution) was added to the filter core, and centrifuged for between 5 and 10 s. A liquid produced in the elution was then discarded.

19) The above step was repeated.

20) The filter core was placed in a new collection tube (provided in the reagent kit). 100 μL of a preheated washing liquid at 95° C. or water not containing nuclease was added to the filter core, and was thereafter centrifuged at a maximum rotational speed for between 20 and 30 s so as to collect a RNA dissolved solution.

Preparation of RT-PCR System for miRNA

| | |
|---|---|
| 2 × SG Green qPCR Mix | 10 μL |
| Forward Primer (10 μM) | 0.4 μL |
| Reverse Primer (10 μM) | 0.4 μL |
| ROX | 0.4 μL |
| cDNA | 1 μL |
| Water, nuclease-free | 7.8 μL |
| Total volume | 20 μL |

Three parallel reaction tubes were provided in order to detect the expression of miRNA, and U6 was adopted as an internal control primer.

Parameters of the PCR program were as follows:
95° C. for 10 min, 45 cycles (95° C. for 15 s, 60° C. for 15 s, 72° C. for 45 s), 95° C. for 15 s, 60° C. for 30 s, and 95° C. for 15 s.

Statistics Analysis

Software OriginPro8.1 was utilized for analysis. The statistical method adopted t-test to perform mean comparison, $P<0.05$ (the difference is significant) and $P<0.01$ (the difference is very significant) were defined to have statistical significance. Expressions of miR-4749-5 and FAS in the adipose tissues of sheep of different varieties were analyzed. The adipose tissue samples extracted from 45 Dorset sheep and 45 Han sheep were numbered and randomly selected to extract the RNA. The expression amounts of miR-4749-5 and FAS were detected, and results indicated that the expression of miR-4749-5 in the adipose tissue of the Dorset sheep was obviously higher than that of the Han sheep, and the former was approximately 2.65 times of the later.

Example 3 Inhibition of Expression of FAS Gene by miRNA

1. Construct of Plasmid and Synthesis of miRNA

A plasmid vector pcDNA3.1 was employed, a green fluorescent protein (GFP) was connected to the vector by EcoRI and NotI, and a 3'UTR sequence of the FAS gene was connected to the vector by restriction sites of XhoI and XbaI to form a vector pcDNA3.1-GFP-3'UTR. The 3'UTR sequence ranges from a first base behind a stop codon of the gene FAS to a last base of mRNA. pcDNA3.1-GFP-3'UTR was sent to a specialized company for synthesizing miR-4749-5, and a synthetic miRNA mimics was then diluted.

2. Experiment Using GFP as Reporter Gene

Mouse fibroblasts was inoculated to a 24-hole plate with a density of $2.5\times10^5$ cells/mL in each hole one day before transfection, and incubated in a DMEM culture solution containing 10% fetal bovine serum for overnight at 37° C., 5% $CO_2$, and saturated humidity until between 70% and 80% cells were merged. The cell culture solution was removed and the cells were washed using a PBS buffer solution preheated to 37° C. for two times, and thereafter cells were transfected. Cells in each hole were added and uniformly mixed with between 200 ng and 500 ng of the vector pcDNA3.1-GFP-3'UTR and 100 nM synthetic miRNA, and were diluted with 100 μL of DMEM excluded from antibodies and serum. In the meanwhile, Liposome 2000 (Lipo-Fectamin™ 2000) transfection reagent was diluted by 100 μL of DMEM excluded from antibodies and serum, and the diluted transfection reagent was added to each hole according to a ratio of 1:2.5. After that DMEM containing the vector, the synthetic miRNA, and the liposome were uniformly mixed, and then incubated for 20 min at the room temperature to form a complex. The complex was added to the cells, slightly mixed, and incubated for 5 hrs at 37° C. and 5% $CO_2$, and a DMEM culture solution was then replaced with a 2% of the fetal bovine serum. 24 hrs and 48 hrs after the transfection, the cells were observed under a fluorescent microscope, and a judge was made according to the GFP positive cell numbers and the intensity of the fluorescence.

3. Results

Fluorescence-positive cells appeared in the transfected cells 24 hrs after the transfection. It is known from results of the fluorescent microscope observation 48 hrs after the transfection that compared with the positive control group which is only transfected by the vector pcDNA3.1-GFP-3'UTR, the number of the GFP-positive cells were significantly reduced in the transfected cell culture medium containing the vector pcDNA3.1-GFP-3'UTR and the synthesized miR-4749-5.

Example 4 Reagent Kit for Detecting miR-4749-5 (Tailing Method)

Reagent kit for extracting a small RNA: mirVana™ miRNA Isolation Kit.
Reverse Transcription and RT-PCR:

| 1 | Reaction solution for reverse transcription | miScript Reverse Transcriptase Mix; miScript HiSpec Buffer; Nucleics Mix; Nuclease-free $H_2O$ |
| 2 | Forward primer SEQID NO: 5 | CCTGTCCCCGCCTTCACCC |
| 3 | Forward internal control primer SEQ ID NO: 6 | CTCGCTTCGGCAGCACA |
| 4 | Reverse internal control primer SEQ ID NO: 7 | AACGCTTCACGAATTTGCGT |
| 5 | Reaction solution for qRT-PCR | 2x LightCycler ® 480 SYBR Green I Master; Universal primer; Nuclease-free $H_2O$ |

Example 5 Reagent Kit for Detecting miR-4749-5 (Stem-Loop Method)

Reagent kit for extracting a total RNA: TRIzol, Invitrogen company in the US.
Reverse Transcription and RT-PCR:

| 1 | RT primer SEQ ID NO: 2 | GTCGTATCCA GTGCAGGGTC CGAGGTATTC GCACTGGATA CGACGGGTGA |
| 2 | Reaction solution for reverse transcription | 5x PrimeScript Buffer2; PrimeScript RT Enzyme Mix; RNase Free $dH_2O$ |
| 3 | Forward primer SEQ ID NO: 3 | TATCCTGTCCCCGCCTTCACCC |
| 4 | Reverse primer SEQ ID NO: 4 | CAGTGCAGGGTCCGAGGTATTC |
| 5 | Reaction solution for qRT-PCR | 2x All-in-one qPCR Mix; Nuclease-free $H_2O$ |

The invention analyzed the high-throughput sequencing results by the bioinformatics method to screen the molecular marker miR-4749-5 applicable for genetic marker-assisted breeding in the meat sheep, and also provided the Q-PCR kit for detecting the expression of miR-4749-5. The reagent kit comprises the whole suit of reagents utilized in experiments including the extraction of RNA, the reverse transcription, and the fluorescence quantitation, thus bring convenience in use, ensuring the consistency of the results, and possessing good application prospect.

The invention claimed is:

1. A method for detecting an expression level of a miRNA comprising the nucleotide sequence of SEQ ID NO: 1 in an adipose tissue of a sheep, the method comprising using a kit for real-time fluorescence quantitative PCR to conduct a tailing method and/or a stem-loop method to detect the expression level of said miRNA in the adipose tissue of the sheep.

2. The method of claim 1, wherein the tailing method for detecting the expression level of said miRNA comprises:
   1) extracting small RNAs from the adipose tissue of the sheep;
   2) tailing and reverse transcribing said miRNA in the small RNAs using a poly(A) polymerase and a reverse transcriptase; and
   3) amplifying said miRNA using a kit for real-time fluorescence quantitative PCR applicable for the tailing method.

3. The method of claim 1, wherein the kit for real-time fluorescence quantitative PCR comprises a specific primer or a primer pair for amplifying said miRNA and a reaction solution for real-time fluorescence quantitative PCR, and wherein the primer pair consists of SEQ ID NO: 3 and SEQ ID NO: 4; and the specific primer is SEQ ID NO: 5.

4. The method of claim 1, wherein the stem-loop method for detecting the expression level of said miRNA comprises:
   1) extracting total RNAs from the adipose tissue of the sheep;
   2) reverse transcribing said miRNA in the total RNAs using a reverse transcription primer and a reverse transcriptase; and 3) amplifying said miRNA using a kit for real-time fluorescence quantitative PCR applicable for the stem-loop method.

\* \* \* \* \*